United States Patent [19]

Gates et al.

[11] 4,263,394
[45] Apr. 21, 1981

[54] AQUEOUS ALKALINE SOLUBLE PHOTOPOLYMERIZABLE MATERIAL

[75] Inventors: Allen P. Gates; Stephen C. Hinch; Christopher V. Withers, all of Leeds, England

[73] Assignee: Vickers Limited, Great Britain

[21] Appl. No.: 49,272

[22] Filed: Jun. 18, 1979

Related U.S. Application Data

[63] Continuation of Ser. No. 753,281, Dec. 22, 1976, abandoned.

[30] Foreign Application Priority Data

Dec. 23, 1975 [GB] United Kingdom .............. 52522/75

[51] Int. Cl.$^3$ .................................................. G03C 1/68
[52] U.S. Cl. .............................. 430/287; 204/159.14; 204/159.22; 525/301; 525/327; 525/386
[58] Field of Search .......................... 260/470 A, 79.1; 526/295, 297, 311, 317, 313, 310, 258, 264; 430/287; 204/159.14, 159.22

[56] References Cited

U.S. PATENT DOCUMENTS

| | | | |
|---|---|---|---|
| 3,799,915 | 3/1974 | Dunnauant et al. | 526/317 |
| 3,993,684 | 11/1976 | Dunnauant et al. | 526/317 |
| 4,065,430 | 12/1977 | Satomura | 526/317 |

*Primary Examiner*—Jack P. Brammer
*Attorney, Agent, or Firm*—Reed, Smith, Shaw & McClay

[57] ABSTRACT

A photopolymerizable material suitable for use in the production of lithographic printing plates comprises a polymer which includes a plurality of structural units represented by the Formula:

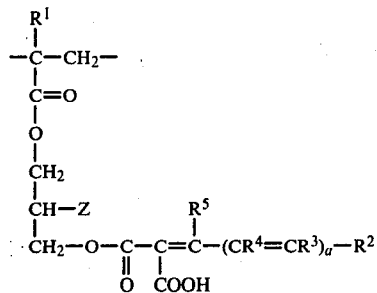

in which $R^1$ represents a hydrogen atom or a methyl group; $R^2$ represents a hydrogen atom, an alkyl or substituted alkyl group, an aryl or substituted aryl group, or a heterocyclic or substituted heterocyclic group; $R^3$, $R^4$ and $R^5$, which may be the same or different, each represents a hydrogen atom, a halogen atom, a cyano group, an alkyl group, an aryl group, an alkoxy group, an aryloxy group, an aralkyl group, an aralkoxy group or an alkoxy carbonyl group; Z represents a hydroxyl group, or an ester group and a is an integer greater than or equal to 1. The polymer may be produced by reacting a polymer of 2,3-epoxy propyl acrylate or 2,3-epoxy propyl methacrylate with an acid of formula

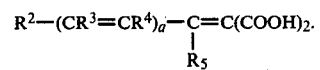

9 Claims, No Drawings

AQUEOUS ALKALINE SOLUBLE PHOTOPOLYMERIZABLE MATERIAL

This is a continuation of application Ser. No. 753,281 filed Dec. 22, 1976, now abandoned.

This invention relates to photopolymerisable materials.

Numerous light-sensitive compositions are known which are based on solvent soluble light-sensitive polymers, such as poly(vinyl cinnamate).

Such a composition for instance when applied in the form of a thin layer to a suitable substrate to form a printing plate or a resist has the disadvantage that after the hardening reaction has occurred under the influence of actinic radiation, an expensive and possibly toxic and/or inflammable solvent is required to remove the unhardened areas.

It is an object of the present invention to provide a photopolymerisable material which, in its un-hardened form, is soluble in an aqueous solution of inorganic salts.

According to one aspect of the present invention, there is provided a photopolymerisable material which comprises a polymer including a plurality of structural units represented by the Formula (I);

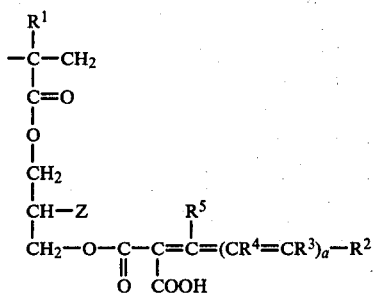

in which $R^1$ represents a hydrogen atom or a methyl group; $R^2$ represents a hydrogen atom, an alkyl or substituted alkyl group, an aryl or substituted aryl group, or a heterocyclic or substituted heterocyclic group; $R^3$, $R^4$ and $R^5$, which may be the same or different, each represents a hydrogen atom, a halogen atom, a cyano group, an alkyl group, an aryl group, an alkoxy group, an aryloxy group, an aralkyl group, an aralkoxy group or an alkoxy carbonyl group; Z represents a hydroxyl group or an ester group; and a is an integer greater than or equal to 1.

According to a preferred feature of the invention, the polymer also includes a plurality of structural units having the Formula (II):

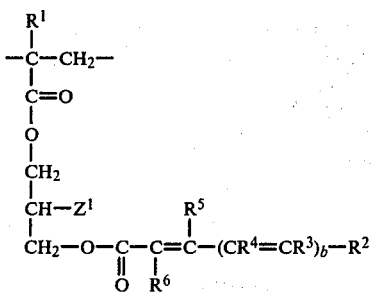

in which $Z^1$ represents a hydroxyl group, an ester group or a halogen atom; $R^1$ to $R^5$ represent the same as in formula I; $R^6$ represents the same as $R^3$ to $R^5$ in Formula I; and in which b is either 0 or an integer greater than or equal to 1.

According to a further preferred feature the polymer also includes a plurality of structural units having the Formula (III):

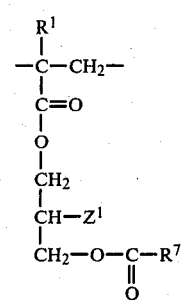

in which $R^1$ represents the same as in Formulae I and II; $R^7$ represents an alkyl or substituted alkyl group, an aryl or substituted aryl group, or a heterocyclic or substituted heterocyclic group; and $Z^1$ represents a hydroxyl group, an ester group or a halogen atom.

According to a further preferred feature, the polymer also includes structural units derived from at least one other unsaturated addition polymerisable monomer.

In the Formulae I and II, $R_2$ may be, for example phenyl, 2-nitrophenyl, 3-nitrophenyl, 4-nitrophenyl, 2-aminophenyl, 3-aminophenyl, 4-aminophenyl, 2 azidophenyl, 3-azidophenyl, 4-azidophenyl, 2-bromophenyl, 3-bromophenyl, 4-bromophenyl, 2-chlorophenyl, 3-chlorophenyl, 4-chlorophenyl, 4-phenylphenyl, 2-methoxyphenyl, 3-methoxyphenyl, 4-methoxyphenyl, 3,4-methylenedioxyphenyl, 2-methylphenyl, 3-methylphenyl, 4-methylphenyl, 2-ethylphenyl 3-ethylphenyl, 4-ethylphenyl, 4-isopropylphenyl, 3,4-dichlorophenyl, 2,4-dichlorophenyl, 2,4-dinitrophenyl, 2-nitro-5-chlorophenyl, 2-3-dimethoxyphenyl; 3,4-dimethoxyphenyl, 2,4-dimethoxyphenyl, 2,5-dimethoxyphenyl, 3,5-dimethoxyphenyl, 2-ethoxyphenyl, 3,4-diethoxyphenyl, 4-dimethylaminophenyl, 4-diethylaminophenyl, 1-naphthyl, 2-naphthyl, 2-ethoxy-1-naphthyl, 2-methoxy-1-naphthyl, 4,8-dimethoxy-1-naphthyl, 2,7-dimethoxy-1-naphthyl, 1-4-dimethoxy-2-naphthyl, 6-methoxy-2-naphthyl, 4-chloro-1-naphthyl, 2-chloro-1-naphthyl, 4-bromo-1-naphthyl, 5-bromo-1-naphthyl, 1-bromo-2-naphthyl, 5-bromo-2-naphthyl, 4-nitro-1-naphthyl, 1-nitro-2-naphthyl, 9-anthranyl, 10-methyl-9-anthranyl, 2-furyl, 5-methyl-2-furyl, 5-bromo-2-furyl, 5-chloro-2-furyl, 5-iodo-2-furyl, 5-nitro-2-furyl, 2-thienyl, 5-bromo-2-thienyl, 3,4-dichloro-2-thienyl, 5-nitro-2-thienyl, 1-methyl-2-pyrrolyl, 2-pyridyl, 3-pyridyl, 4-pyridyl, 6-methyl-2-pyridyl, 4-maleimidophenyl or 4-acetamido phenyl.

Particularly preferred embodiments are: the polymers where, in formula I, $R^2$ represents phenyl and $R^3$, $R^4$ and $R^5$ represent hydrogen; $R^2$ represents 2-nitrophenyl and $R^3$, $R^4$ and $R^5$ hydrogen; $R^2$ represents 3-nitrophenyl and $R^3$, $R^4$ and $R^5$ represent hydrogen; $R^2$ represents phenyl, $R^3$ represents chloro and $R^4$ and $R^5$ represent hydrogen; and $R^2$ represents 4-nitrophenyl, $R^3$ represents chloro and $R^4$ and $R^5$ represent hydrogen; the polymers where, in formula II, and particularly when b=0, $R^2$, $R^5$ and $R^6$ all represent hydrogen; $R^2$ and $R^5$ represent hydrogen and $R^6$ represents methyl; $R^2$ represents phenyl and $R^5$ and $R^6$ represent hydrogen;

$R^2$ represents 4-methoxyphenyl, $R^5$ represents hydrogen and $R^6$ represents cyano; $R^2$ represents 4-chlorophenyl, $R^5$ represents hydrogen and $R^6$ represents phenyl; $R^2$ represents 4-methyl phenyl, $R^5$ is hydrogen and $R^6$ is phenoxy; $R^2$ represents 4-azido phenyl, $R^5$ represents hydrogen and $R^6$ represents cyano; and $R^2$ represents 2-furyl, and $R^5$ and $R^6$ represent hydrogen; the polymers where, in formula II when $b=1$, $R^2$ represents phenyl, $R^3$, $R^4$ and $R^5$ represent hydrogen and $R^6$ is cyano; $R^2$ is phenyl, $R^3$, $R^4$ and $R^5$ represent hydrogen and $R^6$ represents ethoxy carbonyl; and $R^2$ represents phenyl, $R^3$ and $R^4$ represent hydrogen, $R^5$ represents methyl and $R^6$ represents cyano: the polymers where, in formula III, $R^7$ represents methyl and $Z^1$ represents hydroxyl; $R^7$ represents heptyl and $Z^1$ represents hydroxyl; $R^7$ represents ethyl and $Z^1$ represents chlorine; $R^7$ represents trichloromethyl and $Z^1$ represents hydroxyl.

In the case where the polymer also includes structural units derived from another unsaturated addition polymerisable monomer, the monomer may be acrylic or methacrylic acid; an acrylate or methacrylate; a hydroxy acrylate or methacrylate; acrylamide or a substituted acrylamide; methacrylamide or a substituted methacrylamide; acrylonitrile; methacrylonitrile; vinyl chloride; vinyl acetate; styrene or a substituted styrene such as α-methyl styrene, 4-chlorostyrene or p-methoxy styrene; a vinyl ether such as isobutylvinyl ether, 2-chlorovinyl ether, or phenyl vinyl ether; an aliphatic diene, such as chloroprene, butadiene or hexadiene. The presence of such structural units can confer certain desirable advantages, such as better ink receptivity, better abrasion resistance during printing and/or better sensitivity to light.

The polymer in the material of the present invention may be produced by reacting a polymer of 2,3-epoxypropyl acrylate or of 2,3-epoxypropyl methacrylate (either a homopolymer or a copolymer of 2,3-epoxypropyl acrylate or methacrylate with, for example, one of the foregoing monomers) with an ethylenically unsaturated dicarboxylic acid of formula

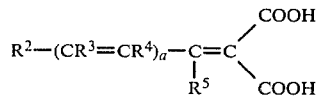

wherein a and $R^2$ to $R^5$ have the above specified meanings. The radiation sensitivity of the polymer in the material of the present invention is provided by the double bonds and its alkali solubility is provided by the unreacted carboxyl groups.

Under suitable conditions, however, the above reaction can be arranged so that not all the epoxy groups of the polymer of 2,3-epoxypropyl acrylate or methacrylate react with the dicarboxylic acid. It is then possible to react these unreacted units with an ethylenically unsaturated monocarboxylic acid (or halide thereof) of formula

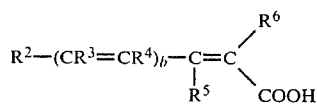

wherein b and $R^2$ to $R^6$ have the above specified meanings to produce structural units of Formula II and/or with a saturated carboxylic acid (or a halide thereof) of formula $R^7$—COOH wherein $R^7$ has the meaning specified above to produce structural units of Formula III. The structural units of Formula II give increased radiation sensitivity without alkali solubility and the structural units of Formula III give increased ink receptivity.

The reaction of the epoxy groups with the acids and acid halides produce structural units containing secondary hydroxyl groups or halogen atoms (represented by Z and $Z^1$ in Formulae I, II and III). In the case where secondary hydroxyl groups are produced, these may advantageously be reacted with a carboxylic acid or ester forming derivative thereof such as the acid halide or anhydride whereby the secondary hydroxyl groups are converted into ester groups. By reacting the secondary hydroxyl groups with the acids used to produce the structural units of Formula II, (or with ester forming derivatives of such acids) increased radiation sensitivity is obtained whereas the use of the acids used to produce the structural units of Formula III (or ester forming derivatives of such acids) will give increased ink receptivity.

Thus, by varying the reactants, and the reaction conditions, it is possible to produce photopolymerisable materials having varying properties in respect of alkali solubility, radiation sensitivity, ink receptivity and abrasion resistance.

Dyes, pigments, leuco dyes, plasticisers and/or sensitisers may be included in the photopolymerisable material which may be coated on to a suitable substrate of, for example, aluminium, to form a radiation sensitive plate for subsequent exposure.

The following Examples illustrate the invention.

Certain of the polymers and carboxylic acids used in the Examples were prepared as described in the following syntheses:

SYNTHESIS A1

Poly (2,3-epoxypropyl methacrylate) α,α'-Azodiisobutyronitrile (8 g) was mixed with 2,3-epoxypropylmethacrylate (200 g) and slowly added to 2-butanone (400 ml) under a nitrogen atmosphere at 70° C. This temperature was maintained for 3 hrs. and then increased to 80° C. for 2 hrs. The cooled solution was diluted with 2-butanone (1400 ml), poured into 40°-60° petroleum ether (12 l) and the product collected and dried to yield 195 g. of poly-(2,3-epoxypropyl methacrylate) having an epoxide equivalent of 158.7.

SYNTHESIS A2

Poly (2,3-epoxypropyl acrylate) α,α'-Azodiisobutyronitrile (0.36 g) was mixed with 2,3-epoxypropyl acrylate (18.0 g) and the solution slowly added to a mixture of 2-butanone (60 ml) and ethanol 20 ml) under a nitrogen atmosphere at 60° C. This temperature was maintained for one hour, raised to 70° C. for two hours and then to 80° C. for a further two hours. The cooled solution was diluted with 2-butanone (100 ml); poured into 40°-60° petroleum ether (1 l) and the product collected and dried to yield 17.2 g of poly-(2,3-epoxypropylacrylate) having an epoxide equivalent of 132.30.

SYNTHESIS A3

Poly(2,3-epoxypropyl methacrylate-co-dodecyl methacrylate). A mixture of 2,3-epoxypropylmethacrylate (16.63 g), dodecyl methacrylate (3.31 g), dodecyl thiol (0.4 g) and α,α'-azodiisobutyronitrile (0.8 g) was polymerised in 2-butanone (50 ml) by the method described in Synthesis A1 to yield 15.2 g of the required co-polymer, having an epoxide equivalent of 178.2.

SYNTHESIS A4

Poly (2,3-epoxypropylmethacrylate-co-styrene). A mixture of 2,3-epoxypropyl methacrylate (18.49 g), styrene (1.51 g), dodecyl thiol (0.8 g) and $\alpha,\alpha'$azodiisobutyronitrile (1 g) was polymerised in 2-butanone (50 ml) by the method described in Synthesis A1 to yield 18.4 g of the required copolymer having an epoxide equivalent of 171.

SYNTHESIS A5

Poly(2,3-epoxypropylacrylate-co-acrylonitrile).

A mixture of 2,3-epoxypropylacrylate (20 g), acrylonitrile (0.92 g), dodecyl thiol (0.4 g) and $\alpha,\alpha'$-azodiisobutyronitrile (0.8 g) was polymerised in a mixture of 2-butanone (50 ml) and ethanol (20 ml) by the method described in Synthesis A2 to yield 20.1 g of the required copolymer having an epoxide equivalent of 145.

SYNTHESIS B1

(i) 3-nitro cinnamaldehyde was prepared by Claisen-Schmidt condensation of 3-nitrobenzaldehyde with acetaldehyde as follows.

A solution of 3-nitrobenzaldehyde (80 g 0.53 mol.) in ethanol (1.6 l) was treated with water (1.8 l). Acetaldehyde (36 ml., 0.644 mol.) was added followed by a 10% aqueous solution of sodium hydroxide (56 ml) and the mixture stirred for 5 hrs at 20° C. The mixture was decanted and the residue boiled with 25% acetic acid (2 l), cooled and the crude product (13.7 g) collected and used without further purification as follows.

(ii) 3-nitro cinnamylidene malonic acid was prepared by reacting 3-nitro cinnamaldehyde (13.7 g) with malonic acid (8.05 g 0.077 mol.) in glacial acetic acid (20 ml) at 100° C. for 6 hrs. After cooling, the product was collected, washed and dried to yield 8.9 g. of the desired product m.p 185°–187° C.

SYNTHESIS B2

Cinnamylidene malonic acid was prepared by reacting cinnamaldehyde (125 g 0.95 mol) with malonic acid (104 g, 1 mol) in glacial acetic acid (200 ml) according to the method described in Synthesis B1(ii) m.p 206°–208° C.

SYNTHESIS B3

2-nitrocinnamylidene malonic acid was prepared by reacting 2-nitro cinnamaldehyde (100 g 0.614 mol) with malonic acid (100 g 0.96 mol.) in glacial acetic acid (95 ml) according to the method described in Synthesis B1 m.p 185°–187° C.

SYNTHESIS B4

(i) $\beta$ chlorocinnamaldehyde was prepared by the following method. Phosphoryl chloride (24 ml, 0.26 mol.) was slowly added to anhydrous dimethyl formamide (40 ml) maintaining a temperature of 0° C. and the resulting solution stirred for 30 minutes. Acetophenone (24 g 0.2 mol.) was also dissolved in anhydrous dimethyl formamide (25 ml) and the mixture slowly added to the phosphoryl chloride solution. Whilst stirring, the reaction mixture was allowed to attain room temperature, stirred for two hours and then poured into an agitated solution of sodium acetate (300 g) in water (750 ml), After stirring for 30 minutes the product was extracted into ether, the ether extracts were dried over magnesium sulphate and the ether was then removed to yield 28.8 g of crude product which was used without further purification as follows.

(ii) $\delta$-chlorocinnamylidene malonic acid was prepared by reacting $\beta$-chlorocinnamaldehyde (16.65 g) with malonic acid (10.4 g) 0.1 mol) in glacial acetic acid (10 ml) according to the method described in Synthesis B1 (ii) to yield 7.5 g of the desired product m.p 158°–160° C. (dec.)

SYNTHESIS B5

(i) 4-nitro-$\beta$-chlorocinnamaldehyde was prepared by a modification of the procedure described in Synthesis B4(i) to yield the desired compound which was recrystallised from ethanol. m.p. 72°–74° C.

(ii) 4-nitro-$\delta$-chlorocinnamylidene malonic acid was prepared by reacting 4-nitro-$\beta$-chlorocinnamaldehyde (80 g 0.39. mol.) with malonic acid (41 g., 0.4 mol). in glacial acetic acid (50 ml) at 100° C. for 6 hours. The cooled solution was poured into a 10% aqueous solution of sodium hydroxide (300 ml), extracted with ether and the aqueous layer acidified with 30% aqueous hydrochloric acid (300 ml) to yield 10.45 g of the desired compound m.p. 173°–175° C.

SYNTHESIS C1

Cinnamylidene-$\alpha$-cyanoacetic acid was prepared by reacting cinnamaldehyde (252 ml 2.0 mol.) with azeotropically dried cyanoacetic acid (170 g., 2.0 mol.) in glacial acetic acid (50 ml) at 100° C. for 2 hrs. Toluene (130 ml) was then added and water removed by azeotropic distillation for a period of 5 hrs. The toluene was distilled off, the reaction mixture cooled and the crystalline product collected, washed with cold glacial acetic acid followed by hot water to yield 235 g. of the desired product m.p. 210°–212° C.

SYNTHESIS C2

4-chloro-$\alpha$-phenyl cinnamic acid was prepared by reacting 4-chlorobenzaldehyde (35 g., 0.25 mol.) with phenylacetic acid (37.4 g 0.275 mol.) in glacial acetic acid (20 ml) at 100° C. for 6 hours. After cooling, the product was collected, washed and dried to yield 31.0 g of the desired compound, m.p. 204°–206° C.

SYNTHESIS C3

4-methyl-$\alpha$-phenoxy cinnamic acid was prepared by reacting 4-methyl benzaldehyde (120 g., 1 mol) with phenoxyacetic acid (167 g., 1.1 mol) in a mixture of acetic anhydride (250 ml 2.5 mol) and triethylamine (101 ml 1 mol) at 140° C. for 5 hours. The cooled deep red solution was poured into 5 liters of a mixture of 1 volume of concentrated hydrochloric acid and 4 volumes of water and the resultant oil separated, washed with water and then with a 20% (w/v) solution of potassium bisulphite (1 liter) to yield the crude product which was collected, washed and recrystalised from aqueous ethanol to give 22 g of the desired compound m.p. 188°–190° C.

SYNTHESIS C4

4-azido-$\alpha$ cyano cinnamic acid was prepared according to the method described in Example 3 of British Specification No. 1,377,747. m.p 160°–160° C. dec.

SYNTHESIS C5

Ethyl hydrogen cinnamylidene malonate was prepared by reacting cinnamaldehyde (31.6 ml 0.2633 mol.) with ethyl potassium malonate (35.7 g 0.26 mol) in glacial acetic acid (5.5 ml) at 100° C. for six hours. After cooling, the product was collected, washed with a little cold acetic acid and then dissolved in water, extracted with ether and the aqueous layer acidified with dilute hydrochloric acid to yield 25.3 g of the desired product.

SYNTHESIS C6

β-(2-furyl) acrylic acid was prepared according to the method described in Organic Syntheses, Collective Vol. III Page 425, 1955. m.p. 140°–141° C.

SYNTHESIS C7

α-cyano-β-methylcinnamylideneacetic acid was prepared by reacting benzylidene acetone (49 g 0.33 mol.) with ethyl cyanoacetate (38 g. 0.33 mol) using, as catalyst, a mixture of ammonium acetate (5 g) and acetic acid (15 g) in benzene (250 ml). The reaction mixture was refluxed and the water of reaction removed by azeotropic distillation for a period of five hours. The cooled solution was washed with water, dried over magnesium sulphate and the solvent evaporated off to yield a yellow crystalline mass.

A solution of potassium hydroxide (7.0 g) in methanol (350 ml) was added and the mixture refluxed for 6 hours, cooled, poured into 30% hydrochloric acid (400 ml) and the precipitate collected and recrystallised from aqueous ethanol to yield 12.34 g of the desired product m.p. 116°–118° C.

EXAMPLE 1

(i) Preparation of a photosensitive, alkali soluble resin 5 g (0.032 mol) of the polymer prepared in synthesis A1 was dissolved in 2-butanone (100 ml) admixed with cinnamylidene malonic acid (synthesis B2) (9.17 g 0.042 mol) and benzyltriethylammonium chloride (0.4 g). The mixture was heated at 80° C. for five hours and then cooled and precipitated into water (2 l). The resultant pale yellow light sensitive polymer was filtered off and dried at 40° C. in air to yield 10:4 g. The acid equivalent was 492.

(ii) Preparation of a printing plate 2 g of the light sensitive polymer was dissolved in 2-butanone (100 ml) coated, by means of a horizontal whirler, on to a sheet of grained and anodised alumiinium and dried by heating at 80° C. for 2 minutes. Exposure of the resultant light sensitive plate to a 4000 watt pulsed xenon lamp through a negative for 2 minutes followed by immersion in a 5.7% aqueous solution of sodium metasilicate resulted in a printing plate from which many satisfactory copies could be taken.

EXAMPLE 2

(i) Preparation of a photosensitive, alkali soluble resin 5 g (0.032 mol) of the polymer prepared in Synthesis A1 was dissolved in 2-butanone (100 ml) and treated with 3-nitrocinnamylidene malonic acid (Synthesis B1) (10.78 g 0.41 mol) and benzyltriethylammonium chloride (0.4 g) and the mixture heated at 80° C. for four hours. Cinnamylidene-α-cyanoacetic acid (Synthesis C1) (25.47 g 0.128 mol) and benzyltriethylammonium chloride (0.4 g) were then added and heating continued a further two hours. The cooled reaction mixture was diluted with an equal volume of 2-butanone, filtered and the filtrates poured into 1,1,1-trichloroethane (1 L) whereupon a polymer separated as a flocculent yellow precipitate which was collected on a filter, sucked dry and redissolved in acetone (100 ml). This solution was poured into a mixture of water (2 L) and concentrated hydrochloric acid (150 ml) and the precipitated resin collected, washed and dried to yield 9.63 g. of the desired product having λmax 317 nm and acid equivalent 446.3.

(ii) Preparation of a Printing Plate 3 g of the above photosensitive resin and 0.3 g of 2,6-dianisyl-4- phenylthiapyrilium perchlorate were dissolved in 2-butanone (100 ml), filtered and applied by means of a horizontal whirler to the surface of a sheet of electro grained and anodised aluminium to give a coating weight of 1 g per square meter. After drying at 80° C. for two minutes, the resultant light sensitive plate was exposed for 40 seconds in a printing down frame in contact with a negative to a 4000 watt pulsed xenon lamp at a distance of 0.65 meters. The exposed plate was developed by swabbing with a 5.7. aqueous solution of sodium metasilicate, rinsed with water and inked with a greasy ink.

EXAMPLE 3

(i) Preparation of a Photosensitive Alkali Soluble Resin

Using the procedure set forth in Example 2 (i) 5 g (0.032 mol) of poly (2,3-epoxypropylmethacrylate) Synthesis A1) were reacted with cinnamylidene malonic acid (Synthesis B2), (8.9 g., 0.041 mol) for two hours and then with 4-chloro-α-phenyl cinnamic acid (Synthesis C2) (16.5 g 0.064 mol) for a further four hours to yield 10.5 g of the required product having λmax 319 n.m and an acid equivalent of 490.4.

(ii) Preparation of a printing plate (a)

3 g of the above photosensitive resin and 0.3 g. of 1,2-benzanthraquinone were dissolved in 2-butanone (100 ml) filtered and applied by means of a whirler to the surface of a sheet of electrograined and anodised aluminium to give a coating weight of 1 g. per square meter. After drying, the resultant light sensitive plate was exposed for 40 secs through a Stouffer stepwedge and developed in the manner described in Example 2 (ii) There was obtained a printing plate with six steps of the stepwedge fully hardened and inked up.

(iii) Preparation of a printing plate (b)

Example 3(ii) was repeated except that crystal violet dye (0.06 g) was additionally included in the coating solution. The presence of a dye in the exposed light sensitive coating was shown to facilitate removal of the unhardened alkali soluble areas by providing a clearly defined, visible image which increased in contrast as the development proceeded.

EXAMPLE 4

(i) Preparation of a photosensitive, alkali soluble resin

Using the procedure set forth in Example 2(i) 5 g (0.032 mol) of poly (2,3-epoxypropyl methacrylate) (Synthesis A1) was reacted with 2-nitrocinnamylidene malonic acid (Synthesis B3) (10.78 g., 0.41 mol.) for two hours and then with 4-methyl-α-phenoxy cinnamic acid (Synthesis C3) (16.25 g 0.064 mol) for a further four hours to yield 8 g. of the required product having λmax 330 n.m, an acid equivalent of 485.2 and containing 2.9% N.

(ii) Preparation of a printing plate 3 g. of the above photosensitive resin and 0.3 g eosin were dissolved in 2-butanone (100 ml) filtered and applied to a sheet of electrograined and anodised aluminium to form a light sensitive plate which was exposed for 2 minutes and processed as in Example 2 (ii). A high quality printing plate was obtained.

EXAMPLE 5

(i) Preparation of a photosensitive, alkali soluble resin

Using the procedure set forth in Example 2(i), 5 g (0.032 mol) of poly(2,3-epoxypropylmethacrylate), (Synthesis A1) were reacted with δ-chlorocinnamylidene malonic acid (Synthesis B4), (10 35 g 0.041 mol.) for three hours and then with 4-azido-α-cyanocinnamic acid (Synthesis C4) (17.55 g, 0.082 mol) for a further three hours to yield 8.4 g of the desired mixed ester resin having λmax 327 n.m, an acid equivalent of 558.5 and containing 1.95% N.

(ii) Preparation of a printing plate 3 g of the above photosensitive resin and 0.03 g of eosin were dissolved in 2-butanone (100 ml), and applied to a sheet of electrograined aluminium to form a light sensitive plate which was exposed for 2 minutes and processed as in Example 2 (ii). A high quality printing plate was obtained.

EXAMPLE 6

(i) Preparation of a photosensitive, alkali soluble resin.

Using the procedure set forth in Example 2(i), 5 g (0.032 mol) of poly(2,3-epoxy propyl methacrylate)(-Synthesis A1) were reacted with 4-nitro-δ-chlorocinnamylidene malonic acid (Synthesis B5), (12.2 g 0.041 mol) for five hours, and then with ethyl hydrogen cinnamylidene malonate (Synthesis C5) (9.68 g, 0.39 mol.) for a further hour to yield 10.025 g. of the desired mixed ester resin having λmax 347 nm and an acid equivalent of 493.4 and containing 2.0% N.

(ii) Preparation of a printing plate 3 g of the above photosensitive resin and 0.3 g of eosin were dissolved in 2-butanone (100 ml), filtered and applied to a sheet of electrograined and anodised aluminium to form a light sensitive plate which was exposed and processed according to the procedure described in Example 2(ii). A high quality printing plate was obtained.

EXAMPLE 7

(i) Preparation of a photosensitive, alkali soluble resin

Using the procedure set forth in Example 2 (i), 5 g (0.032 mol) of poly(2,3-epoxypropyl methacrylate) (Synthesis A1) were reacted with cinnamylidene malonic acid (Synthesis B2) (8.94 g., 0.041 mol) for two hours and then with acrylic acid (9.16 g 0.126 mol.) for a further four hours to yield 12.15 g of the desired mixed ester resin, having an acid equivalent of 501.0.

(ii) Preparation of a printing plate 3 g of the above photosensitive resin and 0.3 g eosin were dissolved in 2-butanone (100 ml) and the filtered solution was applied to a sheet of electrograined and anodised aluminium. The resultant light sensitive plate was exposed for one minute and processed as in Example 2 (ii) to give a high quality printing plate.

EXAMPLE 8

(i) Preparation of a photosensitive, alkali soluble resin

Using the procedure set forth in Example 2(i), 5 g (0.029 mol. epoxide) of poly-(2,3-epoxypropylmethacrylate-co-styrene) (Synthesis A4) were reacted with cinnamylidene malonic acid (Synthesis B2) (8.28 g, 0.038 mol) for two hours and then with β-(2-furyl) acrylic acid (Synthesis C6) (17.4 g, 0.176 mol) for a further four hours to yield 10.6 g of the desired mixed ester resin having an acid equivalent of 469.8.

(ii) Preparation of a printing plate 3 g of the above photosensitive resin and 0.3 g eosin were dissolved in 2-butanone (100 ml) The solution was filtered and applied by means of a whirler to a sheet of electrograined and anodised aluminium to form a light sensitive plate which was exposed for one minute and processed as in Example 2 (ii) to give a high quality printing plate.

EXAMPLE 9

(i) Preparation of a photosensitive, alkali soluble resin

Using the procedure set forth in Example 2 (i) 5 g (0.034 mol. epoxide) of poly(2,3-epoxypropylacrylate-co-acrylonitrile) (Synthesis A5) were reacted with cinnamylidene malonic acid (Synthesis B2) (8.28 g 0.038 mol) for four hours and then with α-cyano-β-methylcinnamylidene acetic acid (Synthesis C7) (16.19 g, 0.076 mol) for a further two hours to yield 9.8 g of the desired mixed ester resin having λmax 321 n.m+an acid equivalent of 531.1.

(ii) Preparation of a printing plate 3 g of the above photosensitive resin and 0.3 g 1,2-benzanthraquinone were dissolved in 2-butanone (100 ml). The solution was filtered and applied by means of a whirler to a sheet of electrograined and anodised aluminium and dried to form a light sensitive plate which was exposed as described in Example 2(ii). The exposed plate was then cut into three equal parts. 1 part was treated with 5.7% aqueous sodium metasilicate solution, rinsed and inked up. 1 part was treated with 2.5% aqueous sodium hydroxide solution, rinsed and inked up. 1 part was treated with 0.033 molar trisodium phosphate solution rinsed and inked up. All three had similar printing capabilities.

EXAMPLE 10

(i) Preparation of a photosensitive, alkali soluble resin 5 g. (0.028 mol) poly (2,3-epoxypropyl methacrylate -co-dodecyl methacrylate) (Synthesis A3) were reacted with cinnamylidene malonic acid (Synthesis B2) (13.74 g 0.063 mol) for 6 hours at 80° C. using triethylamine (0.125 ml) as catalyst for the esterification. The homo-ester resin was isolated by the procedure described in Example 1(i) to yield 8.8 g of the product, having an acid equivalent of 461.6.

(ii) Preparation of a printing plate 3 g of the above photosensitive resin and 0.3 g of eosin were dissolved in 2-butanone (100 ml). The solution was filtered and applied to a sheet of electrograined and anodised aluminium to form a light sensitive plate which was exposed for one minute, developed using a 5.7% aqueous sodium metasilicate solution and rinsed with water. This resulted in a hydrophobic, ink receptive image area due to the incorporation of dodecyl methacrylate units in the substrate polymer chain. The printing plate had excellent printing characteristics.

EXAMPLE 11

(i) Preparation of a photosensitive, alkali soluble resin.

Using the procedure set forth in Example 2 (i) 5 g. (0.032 mol.) of poly(2,3-epoxypropyl methacrylate) (Synthesis A1) were reacted with cinnamylidene malonic acid (Synthesis B2) (8.94 g, 0.041 mol.) for two hours and then with octanoic acid (18.14 g, 0.126 mol) for four hours to yield 10.8 g of the desired mixed ester resin having an acid equivalent of 613.6.

(ii) Preparation of a printing plate

A printing plate was prepared in accordance with the procedure described in Example (ii) and was shown to have similar characteristics due to the incorporation of octanoate ester groups in the photosensitive resin.

EXAMPLE 12

(i) Preparation of a photosensitive, alkali soluble resin 5 g (0.032 mol.) poly (2,3-epoxypropylmethacrylate) (Synthesis A1) and benzyl triethylammonium bromide (0.2 g) were dissolved in 2-butanone (100 ml), treated with propionyl chloride (0.29 g 0.0032 mol) and heated to 80° C. for one hour. Cinnamylidene malonic acid (13.74 g 0.063 mol) and benzyltriethylammonium bromide (0.4 g) were then added and heating continued for a further 5 hours, whereupon the product was isolated by the procedure described in Example 2 (i) to yield 9.1 g of the desired mixed ester resin having an acid equivalent of 422.9, and a chlorine content of 1.97. (w/w).

(ii) Preparation of a printing plate

A printing plate was prepared in accordance with the procedure described in Example 10 (ii). It gave many satisfactory copies without showing signs of wear.

EXAMPLE 13

(i) Preparation of a photosensitive, alkali soluble resin

Using the procedure set forth in Example 2(i) 5 g (0.038 mol epoxide) poly-(2,3-epoxypropyl acrylate) (Synthesis A2) were reacted with cinnamylidene malonic acid (Synthesis B2) (17.0 g, 0.075 mol.) for 2½ hours and then with acetic acid (8.9 cm³, 9.388 g., 0.156 mol.) for a further 3½ hours to yield 10.5 g of the desired mixed ester resin having an acid equivalent of 443.1.

(ii) Preparation of a printing plate (a)

A printing plate was prepared in accordance with the procedure described in Example 4(ii). It was capable of producing many high quality prints without sign of image wear.

(iii) Preparation of a printing plate (b)

A piece of the light sensitive plate prepared as above was exposed for fifteen minutes to a 250 watt tungsten light bulb at a distance of 0.5 m. and then developed and inked as described in Example 2(ii) to give a high quality printing plate.

(iv) Preparation of a printing plate (c).

A further piece of the above prepared, light sensitive plate was exposed to an argon ion laser operating in the ultraviolet to given an exposure of 50 millijoules per square cm. and resulted in a high quality printing plate.

EXAMPLE 14

(i) Preparation of a photosensitive, alkali soluble resin

Using the procedure described in Example 2(i) 15 g (0.096 mol) of poly (2,3-epoxypropyl methacrylate) Synthesis A1) were reacted with cinnamylidene malonic acid (Synthesis B2) (26.8 g 0.123 mol) for four hours and then with trichloroacetic acid (30 g, 0.18 mol.) for a further two hours to yield 31 g of the desired mixed ester having an acid equivalent of 544.1.

(ii) Preparation of a printing plate

A printing plate was prepared in accordance with the procedure described in Example 4(ii). It was capable of producing high quality copies.

EXAMPLE 15

(i) Preparation of a photosensitive, alkali soluble resin 10 g. of the product from Example 14 were dissolved in 2-butanone (100 ml) and treated with acetic anhydride (0.23 g 0.00225 mol) for 4 hours, yielding 9.8 g. of acetylated product.

(ii) Preparation of a printing plate

A printing plate was prepared in accordance with the procedure described in Example 4(ii). It had an extremely hydrophobic image area, and was capable of producing many copies without showing any sign of wear.

We claim:

1. A polymer which includes a plurality of structural units represented by Formula (I):

$$\begin{array}{c} R^1 \\ | \\ -C-CH_2- \\ | \\ C=O \\ | \\ O \\ | \\ CH_2 \\ | \\ CH-Z \quad\quad R^5 \\ | \quad\quad\quad | \\ CH_2-O-C-C=C-(CR^4=CR^3)_a-R^2 \\ \quad\quad\quad || \;\; | \\ \quad\quad\quad O \;\; COOH \end{array}$$

in which $R^1$ represents a hydrogen atom or a methyl group; $R^2$ represents a hydrogen atom, an alkyl or substituted alkyl group, an aryl or substituted aryl group, or a heterocyclic or substituted deterocyclic group; $R^3$, $R^4$ and $R^5$, which may be the same or different, each represents a hydrogen atom, a halogen atom, a cyano group, an alkyl group, an aryl group, an alkoxy group, an aryloxy group, an aralkyl group, an aralkoxy group or an alkoxy carbonyl group; Z represents a hydroxyl group or an ester group and a is an integer greater than or equal to 1, the number of said structural units in the polymer being such that the polymer is photopolymerizable and soluble in aqueous alkaline solution.

2. A polymer as claimed in claim 1, wherein in Formula I, (i) R² represents phenyl and R³, R⁴ and R⁵ represent hydrogen;
(ii) R² represents 2-nitrophenyl and R³, R⁴ and R⁵ represent hgydrogen;
(iii) R² represents 3-nitrophenyl and R³, R⁴ and R⁵ represent hydrogen;
(iv) R² represents phenyl, R³ represents chloro and R⁴ and R⁵ represent hydrogen; or
(v) R² represents 4-nitrophenyl, R³ represents chloro and R⁴ and R⁵ represent hydrogen.

3. A polymer as claimed in claim 1, wherein the polymer additionally includes a plurality of structural units having the Formula (II);

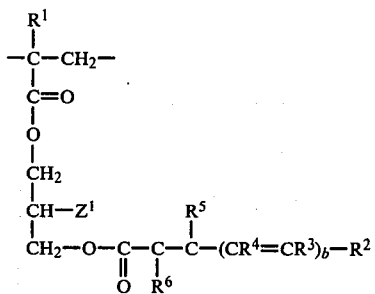

in which $Z^1$ represents a hydroxyl group, an ester group or a halogen atom, $R^1$ to $R^5$ represent the same as in Formula I, $R^6$ represents the same as $R^3$ to $R^5$ in Formula I and b is 0 or an integer greater than or equal to 1.

4. A polymer as claimed in claim 3, wherein in Formula II,
(i) b is 0, and R², R⁵ and R⁶ all represent hydrogen;
(ii) b is 0, R² and R⁵ represent hydrogen; and R⁶ represents methyl;
(iii) b is 0, R² represents phenyl and R⁵ and R⁶ represent hydrogen;
(iv) b is 0, R² represents 4-methoxyphenyl, R⁵ represents hydrogen and R⁶ represents cyano;
(v) b is 0, R² represents 4-chloro-phenyl, R⁵ represents hydrogen and R⁶ represents phenyl;
(vi) b is 0, R² represents 4-methyl phenyl, R⁵ is hydrogen and R⁶ is phenoxy;
(vii) b is 0, R² represents 4-azido phenyl, R⁵ represents hydrogen and R⁶ represents cyano;
(iix) b is 0, R² represents 2-furyl, and R⁵ and R⁶ represent hydrogen;
(ix) b is 1, R² represents phenyl, R³, R⁴ and R⁵ represent hydrogen and R⁶ is cyano;
(x) b is 1, R² is phenyl, R³, R⁴ and R⁵ represent hydrogen and R⁶ represents ethoxy carbonyl; or
(xi) b is 1, R² represents phenyl, R³ and R⁴ represent hydrogen, R⁵ represents methyl and R⁶ represents cyano.

5. A polymer as claimed in claim 1, wherein the polymer additionally includes a plurality of structural units having the Formula (III);

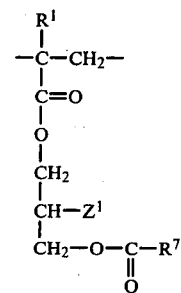

in which $R^1$ and $Z^1$ represent the same as in Formula II and $R^7$ represents an alkyl or substituted alkyl group, an aryl or substituted aryl group, or a heterocyclic or substituted heterocyclic group.

6. A polymer as claimed in claim 5, wherein in Formula III,
(i) R⁷ represents methyl and Z¹ represent hydroxyl;
(ii) R⁷ represents heptyl and Z¹ represents hydroxyl;
(iii) R⁷ represents ethyl and Z¹ represents chlorine; or
(iv) R⁷ represents trichloromethyl and Z¹ represents hydroxyl.

7. A polymer as claimed in claim 1, wherein the polymer additionally includes a plurality of structural units derived from an unsaturated addition polymerisable monomer.

8. A polymer as claimed in claim 7, wherein said polymerisable monomer is dodecyl methacrylate, styrene or acrylonitrile.

9. A light sensitive plate comprising a polymer according to claim 1 coated on a substrate.

* * * * *